United States Patent [19]

Andrus et al.

[11] Patent Number: 4,544,557
[45] Date of Patent: Oct. 1, 1985

[54] 6-(1-HYDROXYETHYL)-2-(2-AMINOETHYL-THIO)-3-TETRAZOLY-1-CARBADETHIAP-EN-2-EM

[75] Inventors: W. Alexander Andrus, Fanwood; Burton G. Christensen, Cliffside Park; James V. Heck, Fanwood, all of N.J.

[73] Assignee: Merck & Co., Inc., Rahway, N.J.

[21] Appl. No.: 539,192

[22] Filed: Oct. 5, 1983

Related U.S. Application Data

[63] Continuation-in-part of Ser. No. 403,190, Jul. 29, 1982, abandoned.

[51] Int. Cl.⁴ .................... C07D 487/04; A61K 31/40
[52] U.S. Cl. ............................ 514/210; 260/245.2 T; 260/245.2 R
[58] Field of Search ................. 260/245.2 R, 245.2 T; 424/274

[56] References Cited

U.S. PATENT DOCUMENTS 3,706,768 12/1972 Bays ..................................... 548/252
3,950,357 4/1976 Kahan et al. .................. 260/245.2 T
4,382,949 5/1983 Afonso .......................... 260/245.2 T

OTHER PUBLICATIONS

Groff; *Essays in Biochemistry*, (John Wiley & Sons, Inc., N.Y.) (1956), pp. 141–155.
McManus et al.; J. Org. Chem., vol. 24, pp. 1462–1464, (1959).
Juby et al.; J. Med. Chem., vol. 11, pp. 111–117, (1968).
Buchanan; J. Med. Chem., vol. 12, pp. 1001–1006, (1969).
English et al., Antimicrobial Agents & Chemotherapy, vol. 10, No. 1, pp. 132–138, (1976).
Andrus et al., JACS, vol. 106, No. 6, 1808, (1984).
Singh et al., Progress in Medicinal Chemistry, vol. 17, 151, (1980).

*Primary Examiner*—Nicholas S. Rizzo
*Attorney, Agent, or Firm*—Thomas E. Arther; Daniel T. Szura; Hesna J. Pfeiffer

[57] ABSTRACT

Disclosed is the antibiotic 6-(1-hydroxyethyl)-2-substituted-thio-3-tetrazolyl-1-carbadethiapen-2-em and its pharmaceutically acceptable salts (I):

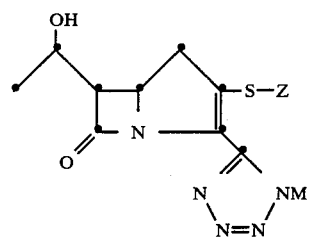

wherein Z is $C_1$–$C_3$ alkylamino, $C_1$–$C_3$ alkylguanidino, $C_1$–$C_3$ alkylamidino, or heterocycloalkyl and, M=H, a synthetically useful cation, or pharmaceutically acceptable cation. Such compounds as well as their pharmaceutically acceptable salts are useful as antibiotics. Also disclosed are processes for the preparation of such compounds; novel intermediates; pharmaceutical compositions comprising such compounds; and methods of treatment comprising administering such compounds and compositions when an antibiotic effect is indicated.

4 Claims, No Drawings

6-(1-HYDROXYETHYL)-2-(2-AMINOETHYLTHIO)-3-TETRAZOLY-1-CARBADETHIAPEN-2-EM

CROSS REFERENCE TO RELATED APPLICATIONS

This application is a continuation-in-part of U.S. application Ser. No. 403,190 filed July 29, 1982, now abandoned.

BACKGROUND OF THE INVENTION

This invention relates to 6-(1-hydroxyethyl)-2-(2-aminoethylthio)-3-tetrazolyl-1-carbadethiapen-2-em (I) and its pharmaceutically acceptable salts which are useful as antibiotics:

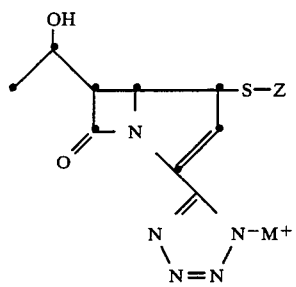

wherein: M is hydrogen; or a pharmaceutically acceptable cation, for example, sodium or potassium, and Z is $C_1$-$C_3$ alkylamino, $C_1$-$C_3$ alkyl guanidino, $C_1$-$C_3$ alkyl amidino, or N-heterocycloalkyl. Preferred definitions of Z are

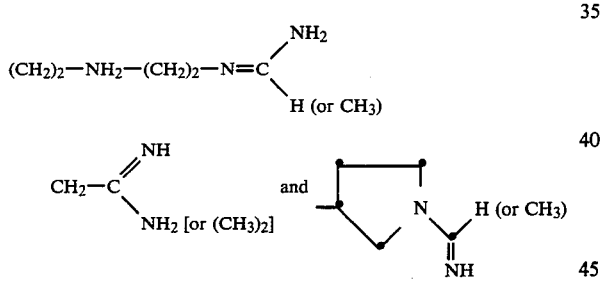

This invention also relates to processes for the preparation of such compounds I; novel intermediates; pharmaceutical compositions comprising such compounds; and to methods of treatment comprising administering such compounds and compositions when an antibiotic effect is indicated.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly, the search for new antibiotics continues.

Thus, it is an object of the present invention to provide a novel class of antibiotics which are useful in animal and human therapy and in inaminate systems. These antibiotics are active against a broad range of pathogens which representatively include both Gram positive bacteria such as S. aureus, Strep. pyogenes, and B. subtilis, and Gram negative bacteria such as E. coli, Pseudomonas, Proteus morganii, Serratia, and Klebsiella. Further objects of this invention are to provide chemical processes for the preparation of such antibiotics and their nontoxic, pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

The compounds of the present invention (Formula I, above) are conveniently prepared by the following scheme.

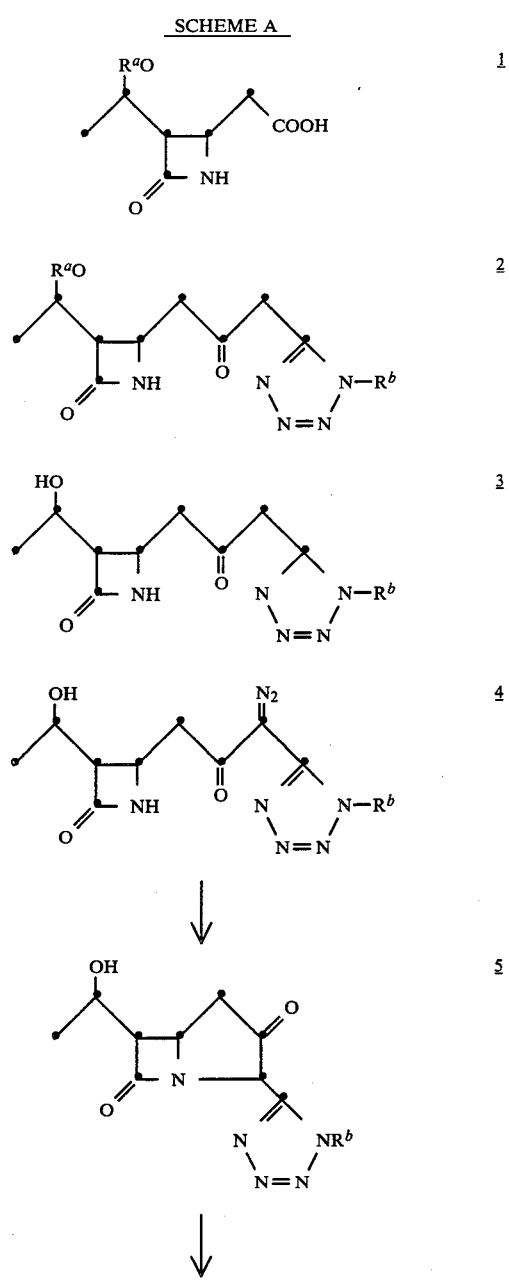

-continued
SCHEME A

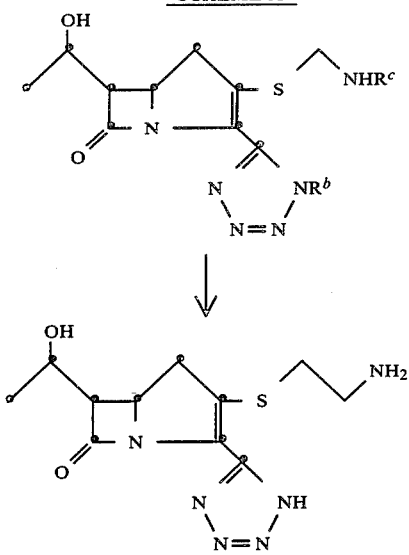

In words relative to the above diagram, azetidinone starting material 1 is known. Relative to azetidinone structure 1, $R^a$ is a readily removable protecting group such as a triorganosilyl function wherein the organo moiety is alkyl, aryl, or aralkyl. Especially preferred protecting groups $R^a$ are such triorganosilyl functions wherein the organo moieties are independently selected from alkyl having from 1–6 carbon atoms, phenyl, and aralkyl having from 7–12 carbon atoms wherein the aryl moiety is phenyl. Especially preferred triorganosilyl groups ($R^a$) include trimethylsilyl, t-butyldimethylsilyl, triethylsilyl, and the like. The transformation 1 to 2 is accomplished by treating 1 in the presence of 1,1'-carbonyldiimidazole, oxalylchloride, phosgene, or the like, in a solvent such as acetonitrile, dimethylformamide (DMF), tetrahydrofuran, dichloromethane, chloroform, or the like, with a reagent 4a (below) calculated to provide the needed chain extension and establish the eventual 3-tetrazolyl moiety. The preparation of reagent 4a is described below. In summary, then, the transformation 1 to 2 is accomplished by treating 1 with 1,1'-carbonyldiimidazole in a solvent selected from acetonitrile, tetrahydrofuran, dimethylformamide, or the like, at a temperature of from 0° to 50° C. followed by treatment with reagent 4a. It should be noted that $R^b$ in structure 2 is a readily removable conventional protecting group selected from the group consisting of benzyl, benzyloxymethyl, p-nitrobenzyl, or the like.

The deprotection of 2 to provide 3 is accomplished by treating 2 in a solvent such as tetrahydrofuran, acetonitrile, dimethylformamide, or the like, at a temperature of from −10° to 30° C. with hydrochloric acid, hydrofluoric acid, sulfuric acid, or the like, for from 1 to 24 hours.

The transformation 3 to 4 is accomplished by treating 3 in a solvent such as chloroform, dichloromethane, acetonitrile, or the like, in the presence of pyridine, triethylamine, potassium, carbonate, or the like, with a diazotizing reagent selected from the group consisting of p-toluene-sulfonyl azide, p-carboxybenzene-sulfonylazide, p-dodecylbenzenesulfonylazide, or the like, at a temperature of from −40° to 20° C. for from 1 to 24 hours.

The transformation 4 to 5 is accomplished by treating 4 in a solvent such as chloroform, dichloromethane, ethyl acetate, or the like at a temperature of from 40° to 80° C. with a catalyst selected from the group consisting of rhodium acetate, rhodium octanoate, cuprous acetate, or the like, for from 1 to 24 hours. The catalysts rhodium acetate and rhodium octanoate are especially preferred.

The transformation 5 to 6 is accomplished by treating 5 in a solvent such as acetonitrile, tetrahydrofuran, dichloromethane, or the like, with a base selected from diisopropylethylamine diazabicycloundecene, triethylamine, or the like, in the presence of trifluoromethanesulfonic acid anhydride (triflic anhydride), p-toluene sulfonic anhydride, diphenylchlorophosphate, or the like, followed by treatment with $HSCH_2CH_2NHR^c$ wherein $R^c$ is a readily removable N-protecting group selected from the group consisting of p-nitrobenzyloxycarbonyl, benzyloxycarbonyl, benzyl, or the like.

The transformation 6 to I is preferably accomplished by hydrogenation wherein 6 in a solvent such as methanol, ethanol, tetrahydrofuran, or the like, at a temperature of from 0° to 20° C. under a hydrogen pressure from 1 to 10 atmospheres in the presence of a hydrogenation catalyst selected from the group consisting of palladium, platinum, rhodium, or the like, is conducted for from 1 to 12 hours.

The previously mentioned reagent utilized in the chain extension and establishment of the tetrazolyl moiety (2 to 3, above) is conveniently prepared by the following scheme.

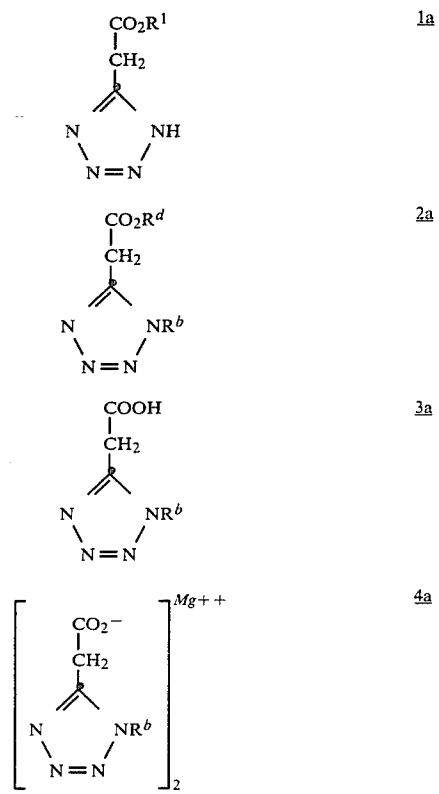

In words relative the above diagram, the transformation 1a to 2a is accomplished by treating 1a in a solvent such as acetonitrile, dimethylformamide, tetrahydrofuran, or the like, in the presence of benzylbromide, benzyloxymethylchloride, p-nitrobenzylbromide, or the like. Relative to starting material 1a, $R^d$ is a ester moiety selected from the group consisting of methyl, ethyl, t-butyl, or the like. Particularly preferred values for $R^d$ include methyl, ethyl, propyl, or the like. A requirement for the precise identity of the value of $R^d$ is that it be easily removed in the subsequent transformation 2a to 3a. Relative to intermediate 2a, $R^b$ is as previously identified and is a readily removable N-protecting group selected from the group consisting of benzyl, benzyloxymethyl, p-nitrobenzyl, and the like.

Transformation 2a to 3a is accomplished by treating 2a in a solvent such as methanol, ethanol, water, or the like, with sodium hydroxide, potassium hydroxide, lithium hydroxide, or the like, at a temperature of from $-20$ to $50°$ C. for from 1 to 24 hours, followed by treatment of with an acid such as hydrochloric, sulfuric, hydrobromic, or the like, to provide 3a.

Transformation 3a to 4a is accomplished by treating 3a with magnesium ethoxide, magnesium methoxide, dibutyl magnesium, or the like, in a solvent such as tetrahydrofuran, acetonitrile, dichloromethane, or the like at a temperature of from $-50°$ to $50°$ C. for from 1 to 6 hours.

A preferred process for preparing the formula I compound features the use of a preferred tetrazole nitrogen blocking group, p-nitrobenzyloxycarbonyloxymethyl having the formula:

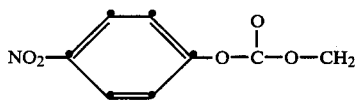

The following equation sequence illustrates this preferred process.

SCHEME B

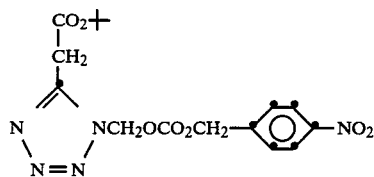

(1) $Et_3CO^-$, $Li^+$, THF
(2) a

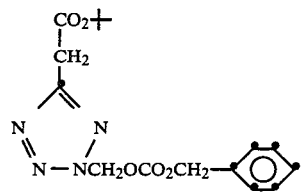

-continued
SCHEME B

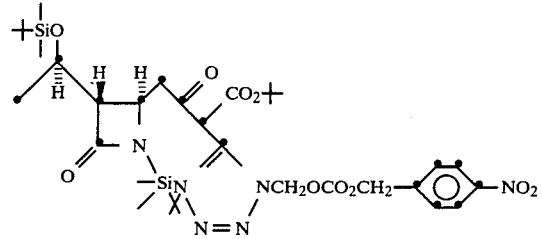

c

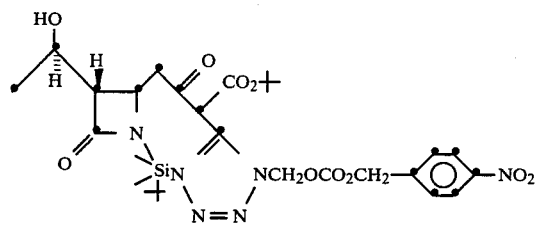

d

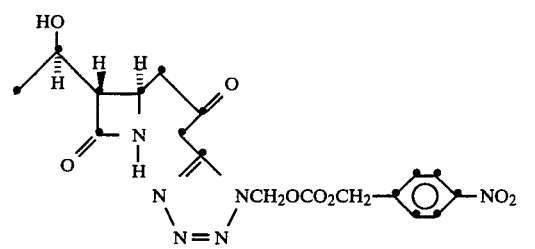

e

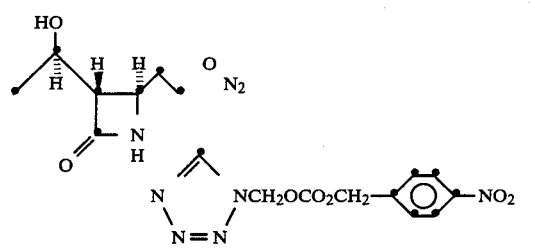

f

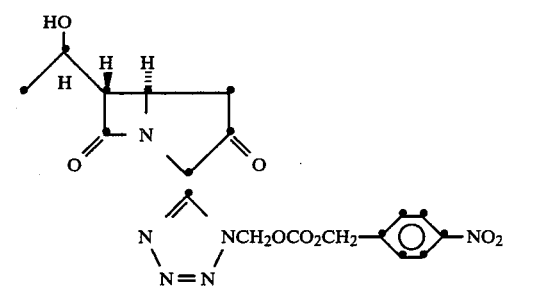

g

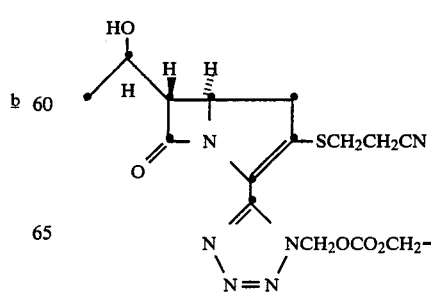

h

-continued
SCHEME B

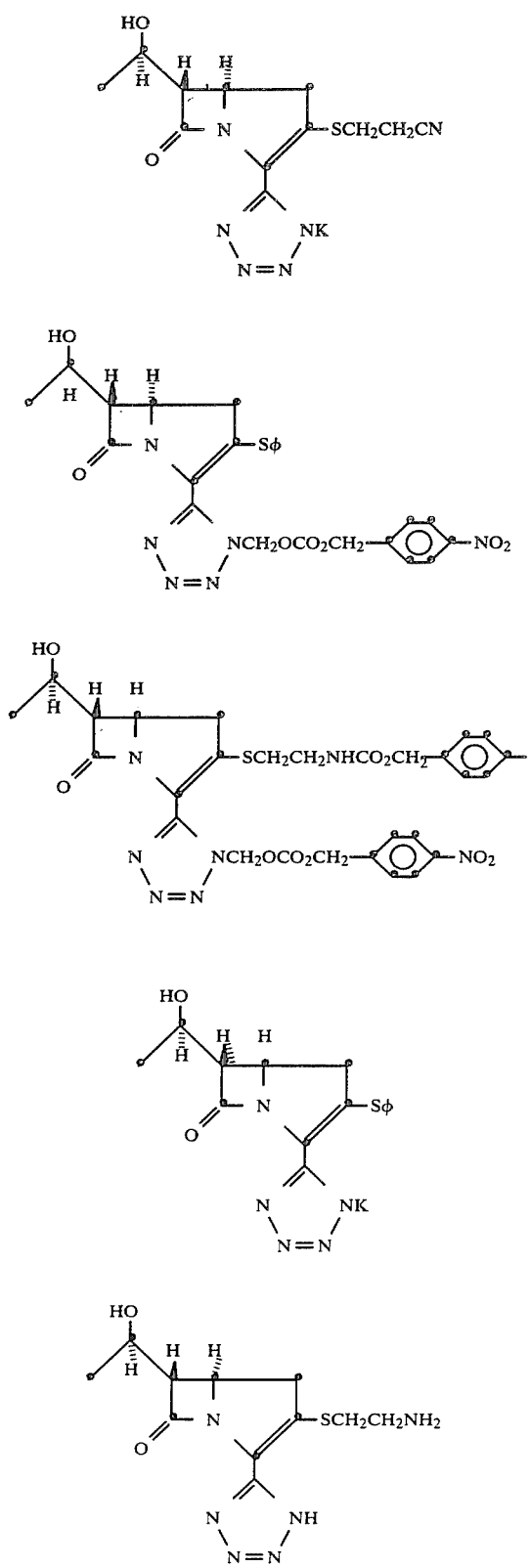

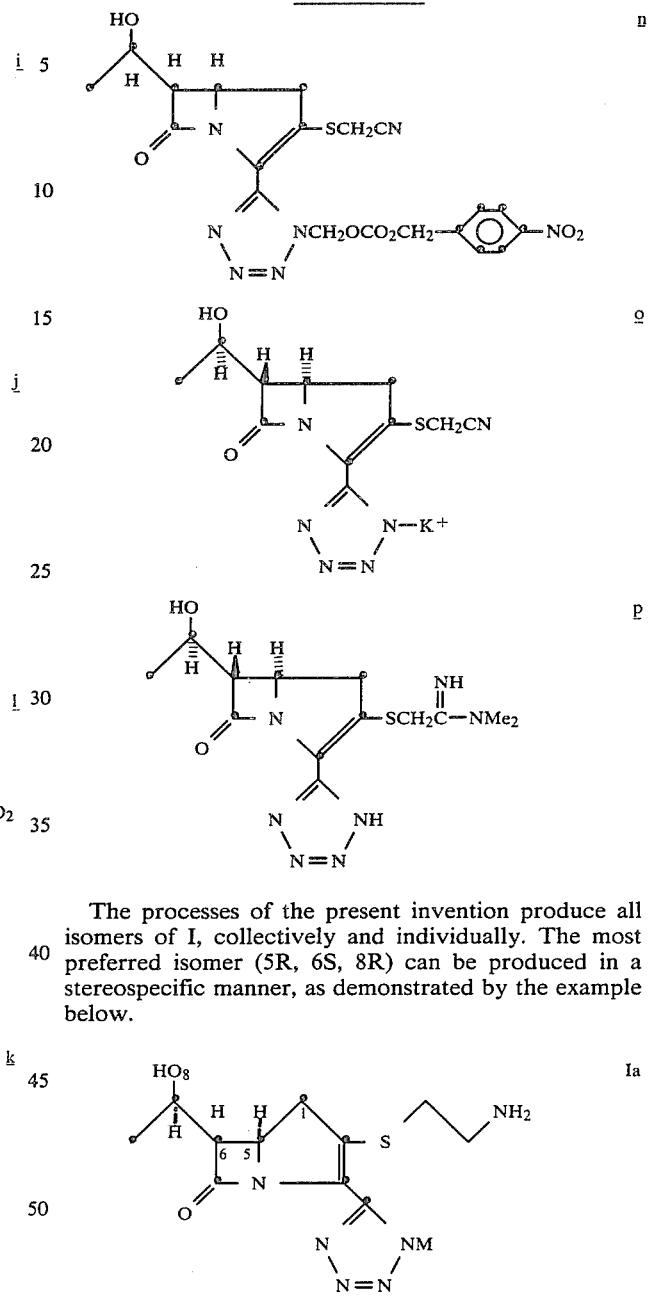

The processes of the present invention produce all isomers of I, collectively and individually. The most preferred isomer (5R, 6S, 8R) can be produced in a stereospecific manner, as demonstrated by the example below.

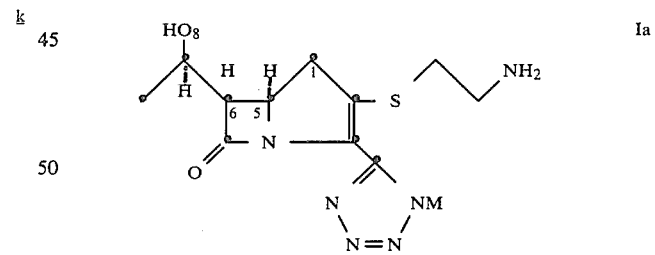

The compounds of the present invention (I) are valuable antibiotics active against various Gram-positive and Gram-negative bacteria and accordingly find utility in human and veterinary medicine. Representative pathogens which are sensitive to antibiotics I include: *Staphylococcus aureus, Escherichia coli, Klebsiella pneumoniae, Bacillus subtilis, Salmonella typhosa, Psuedomonas* and *Bacterium proteus.* The antibacterials of the invention are not limited to utility as medicaments; they may be used in all manner of industry, for example: additives to animal feed, preservation of food, disinfectants, and in other industrial systems where control of bacterial growth is desired. For example they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example, in waterbased paints, and in the white water of paper mills to inhibit the growth of harmful bacteria.

The products of this invention may be used in any of a variety of pharmaceutical preparations. They may be employed in capsule, powder form, in liquid solution, or in suspension. They may be administered by a variety of means; those of principal interest include: orally, topically or parenterally by injection (intravenously or intramuscularly).

Such tablets and capsules, designed for oral administration, may be in unit dosage form, and may contain conventional excipients, such as binding agents, for example, syrup, acacia, gelatin, sorbitol, tragacanth, or polyvinylpyrrolidone; fillers, for example, lactose, sugar, cornstarch, calcium phosphate, sorbitol, or glycerine; lubricants, for example, magnesium stearate, talc, polyethylene glycol, silica; disintegrants, for example, potato starch, acceptable wetting agents such as sodium lauryl sulphate. The tablets may be coated according to methods well known in the art. Oral liquid preparations may be in the form of aqueous or oily suspensions, or solutions, or they may be presented as a dry product for reconstitution with water or other suitable vehicle before use. Such liquid preparations may contain conventional additives such as suspending agents, for example, sorbitol, methyl cellulose, glucose/sugar syrup, gelatin, hydroxyethylcellulose, or carboxymethyl cellulose. Suppositories will contain conventional suppository bases, such as cocoa butter or other glycerides.

Compositions for injection, the preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water.

The compositions may also be prepared in suitable forms for absorption through the mucous membranes of the nose and throat or bronchial tissues and may conveniently take the form of liquid sprays or inhalants, lozenges, or throat paints. For medication of the eyes or ears, the preparation may be presented in liquid or semi-solid form. Topical applications may be formulated in hydrophobic or hydrophilic bases as ointments, creams, lotions, paints, or powders.

The dosage to be administered depends to a large extent upon the condition and size of the subject being treated as well as the route and frequency of administration—the parenteral route by injection being preferred for generalized infections. Such matters, however, are left to the routine discretion of the therapist according to principles of treatment well known in the antibiotic art. In general, a daily dosage consists of from about 5 to about 600 mg of active ingredient per kg. of body weight of the subject in one or more treatments per day. A preferred daily dosage for adult humans lies in the range of from about 10 to 240 mg. of active ingredient per kg. of body weight. Another factor influencing the precise dosage regimen, apart from the nature of the infection and peculiar identity of the individual being treated, is the molecular weight of the chosen species of this invention (I).

The compositions for human delivery per unit dosage, whether liquid or solid, may contain from 0.1% to 99% of active material, the preferred range being from about 10–60%. The composition will generally contain from about 15 mg. to about 1500 mg. of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

In the foregoing word description, it is to be understood that there is considerable latitude in selection of precise reaction parameters. Suggestion of this latitude and its breadth is generally indicated by the enumeration of equivalent solvent systems, temperature ranges, protecting groups, and range of identities of involved reagents.

The following examples recite a precise scheme of synthesis. Example 1 illustrates Scheme A. Example 2 illustrates Scheme B. It is to be understood that the purpose of this recitation is to further illustrate the invention and not to impose any limitation. Temperature is in °C.

EXAMPLE 1

Preparation of 3-(5-tetrazolyl)decarboxylthienamycin

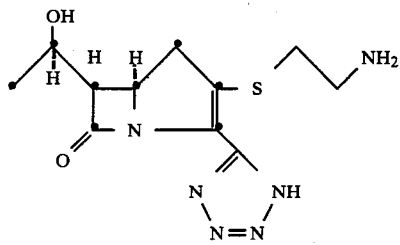

Structures for Example 1

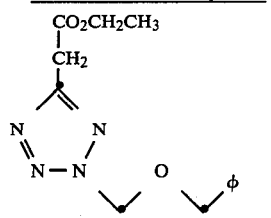

1

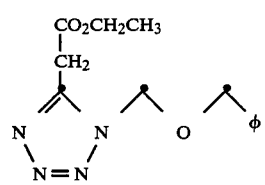

2

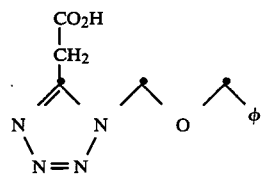

3

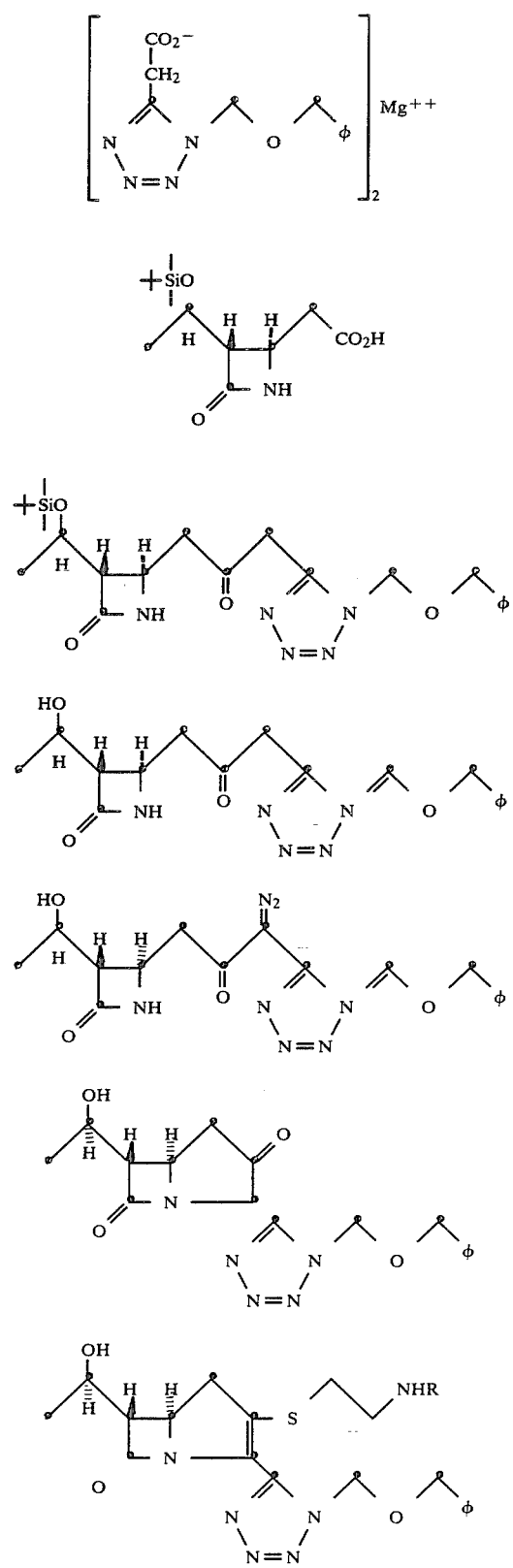

EXAMPLE 1

Preparation of ethyl 5-(1-benzyloxymethyl)tetrazolyl acetate 2 and ethyl 5-(2-benzyloxy-methyl)tetrazolyl acetate 1

Triethylamine (52 ml, 0.37 mol) was added rapidly to ethyl 5-tetrazolylacetate* (48.70 gm, 0.312 mol) in 300 ml acetonitrile at 0°. After 10 minutes stirring, benzylchloromethylether (45.4 ml, 0.33 mol) was added by addition funnel. The mixture was then allowed to warm to room temperature and stir for 16 hours. The resulting mixture was concentrated in vacuo, diluted with 800 ml ethyl acetate and 800 ml diethyl ether, and washed with successive 400 ml solutions of 0.2N sulfuric acid, saturated aqueous sodium bicarbonate, and saturated aqueous sodium chloride. The organic phase was dried over magnesium sulfate, filtered, and concentrated in vacuo to give a pale yellow oil. Chromatography on silica gel (HPLC, ethylacetate: dichloromethane, 1:24) gave, in order of elution, 27.59 gm (32%) ethyl 5-(2-benzyloxymethyl)tetrazolyl acetate 1 and 36.21 gm (42%) ethyl 5-(1-benzyloxymethyl)tetrazolylacetate 2 as colorless oils: 2 IR 1737 cm$^{-1}$ $^1$H NMR (CDCl$_3$)$\delta$ 7.34 (5H, m), 5.85 (2H, S), 4.54 (2H, S), 4.19 (2H, q, J=7), 4.10 (2H, S) mass spectrum 276 (m+).

*Finnegan, W. G., Henry, R. A., Lofquist, R., *J. Amer. Chem. Soc.*, 80, 3908 (1958).

Preparation of 5-(1-benzyloxymethyl)tetrazolylacetic acid 3

A 2.5N sodium hydroxide solution (100 ml, 0.25 mol) was added dropwise over fifteen minutes to ethyl 5-(1-benzyloxymethyl)tetrazolyl acetate 2 (36.21 gm, 0.131 mol) in 800 ml ethanol and 200 ml tetrahydrofuran at room temperature, causing a white precipitate. After one hour, the mixture was concentrated in vacuo. On liter of water was added and the aqueous phase was washed with two 400 ml portions of dichloromethane. The aqueous phase was acidified with 150 ml 2.5N hydrochloric acid and extracted with three 500 ml portions of ethyl acetate. The combined ethyl acetate extracts were dried over magnesium sulfate. Concentration in vacuo and trituration of the white solid from diethyl ether yielded 27.24 gm (84%) 5-(1-benzyloxymethyl)tetrazolylacetic acid 3 as a white solid: mp 125°-126°; $^1$H NMR (CDCl$_3$:DMSO d6, 10:1) $\delta$ 7.40 (5H, m), 5.87 (2H, S), 4.55 (2H, S), 4.09 (2H, S) mass spectrum FD 249 (M+H).

Preparation of magnesium bis-5-(1-benzyloxymethyl)tetrazolylacetate 4

Di-n-butylmagnesium (0.6M in hexane/heptane, 36 ml, 22 mmol) was dripped into a solution of 5-(1-benzyloxymethyl)tetrazolylacetic acid 3 (10.80 gm, 43.5 mmol) and 200 ml tetrahydrofuran at 0°. After addition was complete, the homogeneous solution was concentrated in vacuo, yielding magnesium bis-5-(1-benzyloxymethyl)tetrazolylacetate 4 (12.99 gm) as a white powder; mp>250°. The resulting weight and $^1$H NMR indicated an equivalent of tetrahydrofuran was complexed to the magnesium salt.

Preparation of 1(3S, 4R)-3-[(R)-1-(t-butyldimethylsilyloxy)ethyl]-4-[2-oxo-3-(5-(1-benzyloxy methyl)-tetrazolyl)]propyl-azetidin-2-one 6

To a 10° mixture of (3S, 4R)-3-[(R)-2-(t-butyldimethylsilyloxy)ethyl]-4-acetic acid azetidin-2-one 5 (8.92 gm, 31 mmol), 250 ml dry acetonitrile, and 25 ml, dry N,N-dimethylformamide was added 1,1'-carbonyldiimidazole (5.52 gm, 34 mmol) in one portion. After 90 minutes stirring at room temperature, magnesium bis-5-(1-benzyloxymethyl)tetrazolylacetate 4 (12.99 gm, 22 mmol) was added in one portion. After 4 hours stirring at room temperature, the opaque, greenish mixture was heated at 40° for 16 hours. Concentration in vacuo and diluton with 800 ml ethyl acetate was followed by washing with 400 ml aqueous solutions of cold 0.2N sulfuric acid, saturated sodium bicarbonate, and saturated sodium chloride. The combined aqueous washes were extracted with 600 ml ethyl acetate and washed with the same above sequence of aqueous solutions. The combined organic phases were dried over magnesium sulfate, filtered, and concentrated in vacuo to a viscous, dark oil. Silica gel chromatography (ethyl acetate; dichloromethane, 1:1) gave 10.75 gm (73%) 6 as a colorless foam: IR (CHCl$_3$) 3410, 2950, 1760, 1725 cm$^{-1}$ $^1$H NMR (CDCl$_3$) δ 7.40 (5H, m), 5.88 (1H, brs, NH), 5.79 (2H, S), 4.52 (2H, S), 4.20 (2H, S), 4.18 (1H, m), 3.95 (1H, dt, J=3, 9.5), 3.08 (1H, dd, J=3.5, 18), 2.88 (1H, dd, J=10, 18), 2.80 (1H, dd, J=2, 5), 1.20 (3H, d, J=7), 0.86 (9H, S), 0.06 (6H, d).

Preparation of (3S, 4R)-3-[(R)-1-hydroxyethyl)-4-[2-oxo-3-(5-1-benzyloxymethyl)tetrazolyl)]propyl-azetidin-2-one 7

A 24.5M solution of hydrofluoric acid (1.1 ml, 26 mmol) was added to 6 (3.40 gm, 7.2 mmol) in 20 ml acetonitrile at room temperature. After stirring two hours, 2 ml triethylamine was added. Concentration in vacuo was followed by dilution with 400 ml ethyl acetate and washing with 200 ml aqueous solutions of 0.2N sulfuric acid, saturated sodium bicarbonate, and saturated sodium chloride. The combined aqueous washes were extracted with 300 ml ethyl acetate and washed with the same above sequence of aqueous solutions. The combined organic phases were dried over magnesium sulfate and filtered. Concentration in vacuo caused a precipitation of a white solid. Recrystallization from acetone/diethyl ether yielded 2.22 gm (86%) 7 as white crystals: mp 130°-131°; IR (CH$_3$CN) 3500, 3340, 1760, 1725 cm$^{-1}$ $^1$H NMR (acetone d6) δ 7.37 (5H, S), 6.06 (1H, br S, NH), 5.87 (2H, S), 4.57 (2H, S), 4.47 (2H, S), 4.02 (1H, m), 3.90 (1H, m), 3.22 (1H, dd, J=5.18), 3.08 (1H, dd, J=8, 18), 2.78 (1H, dd, J=2, 7), 1.23 (3H, d, J=7).

Preparation of (3S, 4R)-3-((R)-1-hydroxyethyl)-4-[2-oxo-3-diazo-(5-(1-benzyloxymethyl)tetrazolyl)]propylazetidin-2-one 8

A hexane solution of p-dodecylbenzenesulfonyl azide (0.89M in hexane, 10.6 ml, 9.4 mmol) was added rapidly to 7 (2.60 gm, 7.20 mmol) in 120 ml dichloromethane and 20 ml acetonitrile cooled to −15°. Triethylamine (1.6 ml, 11.5 mmol) was added dropwise to the stirred solution. During the course of two hours, the temperature was allowed to rise to 0°. Concentration in vacuo gave a viscous, dark oil. Chromatography on silica gel (ethyl acetate: dichloromethane, 2:1) yielded 1.87 gm (67%) 8 as a yellow foam: IR (CHCl$_3$) 3410, 2110, 1755–1710, 1650 cm$^{-1}$ $^1$H NMR (CDCl$_3$) δ 7.38 (5H, S), 6.32 (1H, br S, NH), 5.90 (2H, S), 5.59 (2H, S), 4.16 (1H, m), 4.03 (1H, m), 3.16 (2H, m), 2.80 (1H, m), 1.32 (3H, d, J=7).

Preparation of (5R, 6S) 3,7-dioxo-6-((R)-1-hydroxyethyl)-1-azabicyclo[3.2.0]heptane-2-(5-(1-benzyloxymethyl)tetrazole 9

A mixture of 8 (1.85 gm, 4.80 mmol), rhodium acetate dimer (5 mg), and 70 ml dichloromethane was heated to reflux for one hour. After cooling to room temperature, the pink solution was filtered through a pad of magnesium sulfate. Concentration in vacuo yielded 1.57 gm (91%) 9 as a pink foam: IR (CHCl$_3$) 3410, 1772 cm$^{-1}$ $^1$H NMR (CDCl$_3$) δ 7.40 (5H, m), 6.01, 5.87 (2H, AB quartet, J=11), 5.68 (1H, S), 4.45 (2H, S), 4.34 (2H, m), 3.30 (1H, dd, J=2, 6.5), 2.96 (1H, A̲BX, J=7, 18.5), 2.59 (1H, AB̲X, J=8, 18.5), 1.95 (1H, brs, OH), 1.39 (3H, d, J=7 mass spectrum 357 (M+), 327 (—CH$_2$O), 91.

Preparation of (5R, 6S) 3-[2-p-nitro-benzyloxycarbonyl)aminoethylthio]-6-((R)-1-hydroxyethyl)-1-azabicyclo[3.2.0]hept-2-en-7-one-2-(5-(1-benzyloxymethyl)tetrazole 10

1,8-Diazabicyclo[5.4.0]undec-7-ene (0.066 ml, 0.44 mmol) was added to a solution of 9 (0.113 gm, 0.316 mmol) and 8 ml dry tetrahydrofuran at −78°. After stirring 40 minutes, trifluoromethanesulfonic anhydride (0.058 ml, 0.35 mmol) was added. After another 60 minutes, a solution of p-nitrobenzyloxycarbonylaminoethanethiol (0.093 gm, 0.363 mmol) and 0.8 ml dry tetrahydrofuran was added, followed by triethylamine (0.053 ml, 0.38 mmol). The yellow solution was slowly warmed to room temperature and stirred for 18 hours. The solution was diluted with 100 ml ethyl acetate and washed with 50 ml solutions of 5% potassium dihydrogenphosphate and saturated sodium chloride. The organic phase was dried over magnesium sulfate, filtered, and concentrated in vacuo to give a brown oil. Chromatography on silica gel (ethyl acetate: dichloromethane, 4:1) resulted in 0.085 gm (45%) 10 as a yellow solid: IR (CHCl$_3$) δ 3500, 3380, 1780, 1730 cm$^{-1}$ $^1$H NMR (CDCl$_3$) 8.30 (2H, d, J=8), 7.58 (2H, d, J=8), 7.40 (5H, m), 6.18, 5.91 (2H, AB quartet, J=10), 5.64 (1H, t, J=7), NH), 5.22 (2H, S), 4.60 (2H, S), 4.39 (1H, AB X̲, J=3, 8), 4.26 (1H, m), 3.44 (4H, m), 3.32 (1H, dd, J=3, 6.5), 3.10 (2H, m), 1.84 (1H, brs, OH), 1.35 (3H, d, J=7) mass spectrum 595 (m+) UV$_{max}$ (dioxane) 318, 270 nm.

Preparation of 3-(5-tetrazolyl)decarboxythienamycin

A mixture of 10 (0.044 gm, 0.074 mmol), 0.06 gm 20% palladium hydroxide on charcoal, 5 ml n-butanol, 2 ml 0.1M dipotassium hydrogen phosphate/potassium dihydrogen phosphate buffer, and 1 ml ethyl acetate was hydrogenated at 300 psi hydrogen for 4 hours. The mixture was filtered through Celite, eluting with deionized water. The filtrate was washed with 50 ml ether and concentrated in vacuo to give a white powder, with the expected physical properties of 3-(5-tetrazolyl)-decarboxythienamycin 11.

EXAMPLE 2

Step A:

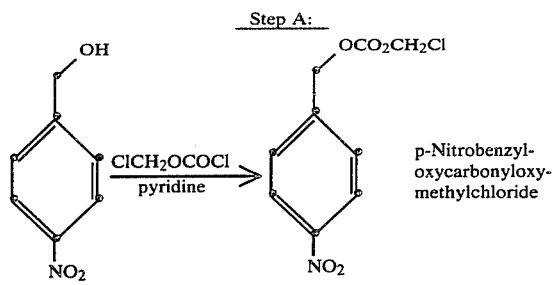

p-Nitrobenzyl alcohol (30.6 g, 200 mmoles) was dissolved in 160 ml dry tetrahydrofuran and 16.2 ml (200 mmoles) pyridine and the solution was cooled to 0°. Chloromethyl chloroformate (17.0 ml, 200 mmoles) in 25 ml ether was added dropwise with stirring over 30 minutes. When the addition was complete the bath was removed and the mixture was stirred 1 hour at room temperature. The mixture was then diluted with ether (300 ml), the precipitated pyridine hydrochloride was filtered and the filtrate evaporated to yield 45 g of crude product. Purification was effected by chromatography on 1000 ml silica gel with an ether-hexanes gradient to yield 17.1 g of pure p-nitrobenzyl chloromethylcarbonate (34.9% yield).

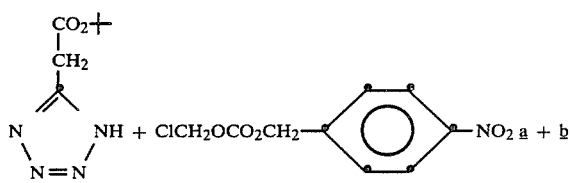

Step B: Preparation of tert-butyl 5-(1-p-nitrobenzyloxycarbonyloxymethyl)tetrazolyl acetate a and tert-butyl 5-(2-p-nitrobenzyloxycarbonyloxymethyl)tetrazolyl acetate b Triethylamine (8.8 ml, 0.063 mol) was added to tert-butyl 5-tetrazolylacetate (7.64 gm, 0.042 mol) in 50 ml acetonitrile at 5°. p-Nitrobenzyloxycarbonyloxymethylchloride (9.10 gm, 0.037 mol) was added in one portion. After warming to room temperature and stirring under nitrogen for 16 hours, the solution was heated to 60° for one hour. After cooling to 0°, 100 ml diethylether was added and stirred for 10 minutes. Triethylammonium chloride crystals were filtered. Solvent removal in vacuo of the eluate gave an orange oil. Chromatography on silica gel (ethyl acetate:hexane, 1:3) gave, in order of elution, 7.35 gm (51%) b and 5.42 gm (37%) a as colorless oils. Trituration of a with diethylether gave crystals: m.p. 72°–76° IR (CHCl$_3$) 1760, 1725, 1525 cm$^{-1}$.

$^1$H NMR (CDCl$_3$)δ 8.26 (2H, d, J=9), 7.52 (2H, d, J=9), 6.37 (2H, s), 5.30 (2H, s), 4.17 (2H, s), 1.45 (9H, s);

Calc'd: C, 48.86; N, 17.80; H, 4.86, Found: C, 49.13; N, 17.55; H, 4.85.

a c

Step C: Preparation of (3S,4R)-1-t-butyldimethylsilyl-3-[(R)-1-(t-butyldimethylsilyloxy)-ethyl]-4-[2-oxo-3-t-butylcarboxy-3-(5-(1-p-nitrobenzyloxycarbonyloxymethyl)tetrazolyl)]-propyl-azetidin-2-one c A heterogeneous mixture of (3S,4R)-1-t-butyldimethylsilyl-3-[(R)-2-(t-butyldimethylsilyloxy)ethyl]-4-acetic acid azetidin-2-one (2.07 gm, 5.17 mmol), sodium carbonate (0.60 gm, 5.69 mmol), 10 ml tetrahydrofuran and 2 ml acetonitrile was heated at 50° for one hour. After cooling to room temperature, the solvent was removed under vacuum. The resulting solid was suspended in 50 ml dichloromethane, 0.01 ml dimethylformamide, and cooled to −15°. Oxalyl chloride (0.54 ml, 6.20 mmol) was added dropwise by syringe, causing vigorous gas evolution. The orange solution was maintained at −15° and used within several hours. In a separate flask, a (1.83 gm, 4.65 mmol) was dissolved in 20 ml tetrahydrofuran and cooled to −78°. A hexane solution of lithium triethylcarboxide (8.7 ml, 1.07 molar, 9.31 mmol) was added by syringe, effecting a brownish-orange solution. After 10 minutes at −78°, the −15° solution of (3S,4R)-1-t-butyldimethylsilyl-3-[(R)-2-(t-butyldimethylsilyloxy)ethyl]-4-acetyl chloride azetidin-2-one was transferred rapidly by cannula, followed by rinsing with 10 ml dichloromethane. After 45 minutes at −78°, 10 ml of pH 7, 0.1M potassium phosphate buffer was added to the brownish-orange solution, causing it to lighten. The mixture was diluted with 500 ml diethylether and washed with 100 ml aqueous solutions of 5% KH$_2$PO$_4$, saturated sodium bicarbonate, and saturated sodium chloride. The organic layer was dried over magnesium sulfate, filtered, and concentrated under vacuum to a yellow oil. Silica gel chromatography (ethyl acetate:hexane, 1:3) gave 2.366 gm (66%) c as a white solid: m.p. 113°–18° IR (CHCl$_3$) 1760, 1740, 1525 cm$^{-1}$. $^1$H NMR (CDCl$_3$)δ 8.29 (2H, d, J=8), 7.56 (2H, d, J=8), 6.20 (2H, AB quartet, J=8), 5.31 (2H, 5), 4.18 (1H, m), 3.98 (1H, m), 3.05 (1H, dd, J-2.5, 4.5), 2.86 (1H, dd, J=4.5, 14.5), 2.62 (1H, dd, J=9, 14.5), 1.41 (9H, s), 1.18 (3H, d, J=7), 0.88 (18H, 5), 0.16 (3H, s), 0.10 (3H, s), 0.07 (3H, s), 0.05 (3H, s).

c→d

Step D: Preparation of (3S,4R)-1-tert-butyldimethylsilyl-3-[(R)-1-hydroxyethyl)-4-[2-oxo-3-(5-(1-paranitrobenzyloxycarbonyloxymethyl)tetrazol-yl)]propyl-azetidin-2-one d Trifluoroacetic acid (15 ml) was added to c (1.40 gm, 1.8 mmol) in 20 ml dichloromethane at 0°.

The solution was allowed to warm to room temperature and stirred under nitrogen for 6 hours. After 20 ml toluene was added, the volatiles were removed under a stream of nitrogen. Total solvent removal under vacuum left an oil which was triturated with ether to give d as a white solid:

$^1$H NMR (CDCl$_3$) δ 8.18 (2H, d, J=8), 7.48 (2H, d, J=8), 6.18 (2H, s), 5.20 (2H, s), 4.30 (2H, s), 4.0 (2H, m), 3.9 (3H, m), 1.20 (3H, d, J=7), 0.92 (9H, s), 0.18 (3H, s), 0.14 (3H, s).

d→e

Step E: Preparation of (3S,4R)-3-[(R)-1-hydroxyethyl]-4-[2-oxo-3-(5-(1-paranitrobenzyloxycarbonyloxymethyl)tetrazolyl)]propylazetidin-2-one d A 24.5M solution of hydrofluoric acid (0.5 ml, 12 mmol) was added to d (0.89 gm, 1.6 mmol) in 12 ml acetonitrile at −10°. The pale yellow solution was stored at −10° for 18 hours, the diluted with 300 ml ethyl acetate. After washing with 0.1M pH 7 phosphate buffer and saturated sodium chloride solutions, the organic phase was dried over magnesium sulfate and filtered. Removal of solvent under vacuum gave e (0.72 gm, 1.6 mmol) as a yellow oil which solidified on standing:

$^1$H NMR (acetone d6) δ 8.29 (2H, d, J=9), 7.73 (2H, d, J=9), 7.17 (1H, br s), 6.44 (2H, s), 4.60 (2H, s), 4.04 (1H, m), 3.86 (1H, m), 3.30 (1H, dd, J=5, 18), 3.15 (1H, dd, J=9, 18), 2.83 (1H, dd, J=2, 7), 1.23 (3H, d, J=7).

e→f

Step F: Preparation of (3S,4R)-3-[(R)-1-hydroxyethyl]-4-[2-oxo-3-diazo-(5-(1-paranitrobenzyloxycarbonyloxymethyl)tetrazolyl)]-propylazetidin-2-one f A hexane solution of paradodecylbenzenesulfonylazide (0.89M, 2.5 ml, 2.2 mmol) was added rapidly to e (0.72 gm, 1.6 mmol) in 80 ml dichloromethane at −15°. Triethylamine (0.40 ml, 2.7 mmol) was added dropwise to the stirred solution. After one hour, the solvent was removed under vacuum. Chromatography of the dark oil on silica gel gave 0.302 gm, 0.64 mmol f (35% yield from c) as a yellow foam:

IR (CHCl$_3$) 3420, 2120, 1760, (br), 1660 cm$^{-1}$. $^1$H NMR (CDCl$_3$) δ 8.26 (2H, d, J=9), 7.54 (2H, d, J=9), 6.51 (2H, AB quartet, J=10), 6.25 (1H, br s), 5.29 (2H, s), 4.20 (1H, m), 4.20 (1H, m), 4.10 (1H, m), 3.16 (1H, dd, J=5.5, 17), 3.02 (1H, dd, J=8, 17), 2.86 (1H, dd, J=2, 6.5), 1.34 (3H, d, J=6.5).

f→g

Step G: Preparation of (5R,6S) 3,7-dioxo-6-[(R)-1-hydroxyethyl]-1-azabicyclo[3.2.0-]heptane-2-(5-(1-paranitrobenzyloxycarbonyloxymethyl)-tetrazole g A mixture of f (0.290 gm, 0.61 mmol), rhodium acetate dimer (2 mg), and 35 ml dichloromethane was heated at reflux for one hour. After cooling to room temperature, the pink solution was filtered through a pad of magnesium sulfate, eluting with tetrahydrofuran. Solvent removal under vacuum gave 0.243 gm, 0.54 mmol g (89%) as an off-white solid: $^1$H NMR (CDCl$_3$)δ 8.25 (2H, d, J=9), 7.56 (2H, d, J=9), 6.47 (2H, AB quartet, J=11), 5.85 (1H, s), 5.30 (2H, s), 4.38 (1H, m), 4.30 (1H, m), 3.32 (1H, dd, J=2, 6.5), 3.06 (1H, dd, J=7, 19), 2.69 (1H, dd, J=7.5, 19), 1.38 (3H, d, J=6.5).

g→h

Step H: Preparation of (5R,6S) 3-(2-cyanoethylthio-6-[(R)-1-hydroxyethyl]-1-azabicyclo[3.2.0]-hept-2-en-7-one-2-(5-(1-para-nitrobenzyloxycarbonyloxymethyl)tetrazole h 1,8-Diazabicyclo[5.4.0]undec-7-ene (0.021 ml, 0.14 mmol) was added to a solution of g (0.047 gm, 0.105 mmol) and 5 ml dry tetrahydrofuran at −78°. After stirring 20 minutes, trifluoromethanesulfonic anhydride (0.021 ml, 0.13 mmol) was added. After another hour, 3-mercaptopropionitrile (0.010 ml, 0.13 mmol) and triethylamine (0.018 ml, 0.14 mmol) were added. The yellow solution was slowly warmed to 0° and stirred for 2 hours. After dilution with 100 ml ethyl acetate, the solution was washed with 50 ml solutions of 5% potassium dihydrogen phosphate, saturated sodium bicarbonate, and saturated sodium chloride. The organic phase was dried over magnesium sulfate, filtered, and concentrated under vacuum to give a brown oil. Chromatography on silica gel (ethyl acetate:dichloromethane, 2:1) resulted in 0.009 gm (17%) h as a white solid:

$^1$H NMR (CDCl$_3$) 8.27 (2H, d, J=9), 7.57 (2H, d, J=9), 6.64 (2H, AB quartet, J=11), 5.29 (2H, s), 4.41 (1H, qd, J=3, 8), 4.28 (1H, quintet, J=6), 3.02–3.53 (4H, m), 2.67–2.80 (2H, m), 1.35 (3H, d, J=6). UV λ$_{max}$ (dioxane) 316, 262 nm.

g→n

Step I: Preparation of (5R,6S)-2-cyanomethylthio-6-(R-1-hydroxyethyl)-1-azabicyclo[3.2.0]-hept-2-en-7-one-2-(5-(1-para-nitrobenzyloxycarbonyloxymethyl)tetrazole n 1,8-Diazabicyclo[5.4.0]undec-7-ene (0.045 ml, 0.30 mmol) was added to a solution of g (0.111 gm, 0.249 mmol) and 5 ml dry tetrahydrofuran at −78°. After stirring 20 minutes, trifluoromethanesulfonic anhydride (0.050 ml, 0.30 mmol) was added. After 40 minutes, the solvent was removed under vacuum at −20°. Dissolution of the residue in 1.5 ml dry dimethylformamide and cooling to −20° was followed by the addition of sodium hydrogen sulfide (0.017 gm, 0.30 mmol) as a solid and diisopropylethylamine (0.052 ml, 0.30 mmol). After 2 hours at −20°, chloroacetonitrile (0.057 ml, 0.90 mmol) and diisopropylethylamine (0.052 ml, 0.30 mmol) were added. The solution was allowed to warm to room temperature and stirred for 3 hours. After dilution with 100 ml ethyl acetate, the solution was washed with 50 ml solutions of 5% potassium dihydrogen phosphate, saturated sodium bicarbonate, and saturated sodium chloride. The organic phase was dried over magnesium sulfate, filtered and concentrated to give a brown oil, which was chromatographed on silica gel to give 0.041 gm (33%) n as a white solid:

$^1$H NMR (CDCl$_3$)δ 8.25 (2H, d, J=9), 7.56 (2H, d, J=9), 6.64 (2H, AB quartet, J=11), 5.29 (2H, s), 4.47 (1H, qd, J=3, 8), 4.31 (1H, m), 3.68 (2H, AB quartet, J=18), 3.49 (1H, dd, J=10, 18), 3.43 (1H, dd, J=3, 5), 3.37 (1H, dd, J-8, 18), 1.35 (3H, d, J=6). UV λ$_{max}$ (dioxane) 313, 264 nm.

h→i

Step J: Preparation of Potassium (5R,6S)-2-(2-cyanoethyl)thio-6-(R-1-hydroxyethyl)-3-(5-tetrazolyl)-carbapenem i A mixture of h (0.012 gm, 0.023 mmol), 0.02 gm 10% palladium on carbon, 0.6 ml 0.1M dipotassium hydrogen phosphate/potassium dihydrogen phosphate buffer, 1.2 ml tetrahydrofuran, and 0.6 ml ethanol was hydrogenated at 45 psi hydrogen for one hour. The mixture was filtered through Celite, eluting with deionized water. The filtrate was washed with 20 ml diethylether and concentrated under vacuum to a volume of 1.5 ml at 0°. Reverse phase prep TLC chromatography (1.5% THF in H$_2$O) allowed isolation of a single band at R$_f$6. The silica was eluted with 4:1/acetonitrile:water and washed with 3×20 ml portions of hexane. Concentration of the aqueous phase and lyophilization gave 0.008 gm (100%) i as a white powder:

$^1$H NMR (D$_2$O) δ 4.5–4.2 (2H, m), 3.48 (1H, dd, J=3, 5.5), 3.37 (1H, dd, J=10, 17), 3.16 (1H, dd, J=8, 17), 3.21 (1H, dd, J=7, 14), 2.98 (1H, dd, J=7, 14), 2.76 (2H, qd, J=7, 12), 1.25 (3H, d, J=6.5). UV λ$_{max}$ (H$_2$O) 294 nm.

g→j

Step K: Preparation of (5R,6S)-2-phenylthio-6-(R-1-hydroxyethyl)-1-azabicyclo[3.2.0]hept-2-en-7-one-2-(5-(1-para-nitrobenzyloxycarbonyloxymethyl)tetrazole j Bicyclic ketotetrazole g (37 mg, 0.083 mmole) was dissolved in 2.0 ml dry tetrahydrofuran, cooled to −78° and 14 μl (0.091 mmole, 1.1 eq.) of 1,5-diazabicyclo[5.4.0]undec-5-ene (DBU) was added. The yellow solution was stirred for 5 minutes at −78° and then 15 μl (0.09 mmole, 1.1 eq.) of trifluoromethane sulfonic anhydride was added. The mixture was stirred and allowed to warm to −20° over 90 minutes, at which point the formation of the enol triflate was nearly complete by tlc and UV. The solution was again cooled to −78° and 9 μl (0.082 mmole) of benzenethiol and 12 μl (0.086 mmole) of triethylamine were added. The solution was allowed to warm to room temperature over 1 hour and then diluted with 15 ml ethyl acetate and quenched with 5 ml pH 4 phosphate buffer. The organic phase was washed with brine, dried over sodium sulfate and concentrated to yield 45 mg of a crude product which was purified by chromatography on 7 ml silica gel packed in 40% ethyl acetate in hexanes and eluted with a 40% 60% gradient to yield carbapenem j (11 mg, 24.6% yield).

UV λ$_{max}$ 321 nm (=9200) 264 nm (=10,200)
IR (CHCl$_3$) 1770 cm$^{-1}$
NMR (CDCl$_3$) δ CH$_3$ 1.24 (d), C-1 CH$_2$ 2.84 (app. doub.), H$_6$ 3.22 (dd), H$_3$ H$_8$ (4.2 (m) PNB CH$_2$ 5.32 (S), NCH$_2$OCO$_2$, 6.70 (AB), PNB+Sφ, 7.34, 7.60, 8.24 (m).

g→l

Step L: Preparation of (5R,6S)-2-(2-(N-para-nitrobenzyloxycarbonyl)aminoethylthio)-6-(R-1-hydroxyethyl)-1-azabicyclo[3.2.0]hept-2-en-7-one-2-(5-(1-para-nitrobenzyloxycarbonyloxymethyl)tetrazole l Bicyclic ketotetrazole g (41 mg, 0.092 mmole) was dissolved in 2.0 ml dry tetrahydrofuran and cooled to −78°. DBU (1,5-diazabicyclo[5.4.0]-undec-5-ene (15 μl, 0.10 mmole) was added and the solution was stirred 5 minutes. Trifluoromethanesulfonic anhydride (17 μl, 0.01 mmole) was added and the mixture allowed to warm to −20° over 90 minutes. The resulting enoltriflate solutionn was recooled to −78° and a solution of N-(p-nitrobenzyloxycarbonyl)-cysteamine (22 mg, 0.086 mmole) and triethylamine (15 μl, 0.107 mmole) in 0.50 ml tetrahydrofuran was added. The reaction mixture was allowed to warm to 0° over 2 hours, then held at 0° for an additional 2 hours. Workup was effected by dilution with ethyl acetate, washing with pH 4 phosphate buffer and brine, drying over sodium sulfate and concentration to yield 63 mg crude product. Chromatography on 10 ml silica gel with an ethyl acetate-hexanes gradient afforded 14 mg (22% yield) of protected tetrazolyl thienamycin, l.

UV (THF) λ$_{max}$ 322 nm (8000), 265 (=17000)
NMR (d$_6$ acetone) 1.26 (d) CH$_3$, 3.5 (m, 7H), 4.2 (dq) H$_8$, 4.4 (ddd) H$_5$ 5.34 (s) PNBCH$_2$, 3.42 (s) PNBCH$_2$, 6.75 (s) NCH$_2$ OCO$_2$, 7.70 (2d) Ar, 8.25 (2d) Ar.

j→k

Step M: Preparation of Potassium (5R,6S)-2-phenylthio-6-(R-1-hydroxyethyl)-3-(5-tetrazolyl)-carbapenem k The blocked carbapenem j (10 mg, 0.0185 mmole) was dissolved in 2.0 ml tetrahydrofuran and 0.4 ml ethanol, 0.5 ml water, 0.1 ml 1M pH 7 phosphate buffer and 20 ml 10% palladium on charcoal were added. This mixture was hydrogenated at 50 psi for 90 minutes (Parr shaker) at which point the reaction was complete by UV. The mixture was diluted with 2 ml water and 100 μl pH 7 buffer (final pH 6.9), filtered through Celite containing a small amount of activated charcoal and the residue washed with 2×1 ml water. The combined filtrates were extracted with 2×5 ml ether, the organics backwashed with 1.0 ml water and the combined aqueous phases concentrated at 1 mm (20°) to remove THF and ethanol. The residual aqueous was partially lyophilized to a volume of 1.5 ml, which was applied to 6 0.5 mm Analtech reversed phase TLC plate and the plate developed with 5% aqueous tetrahydrofuran. The major UV-active band (R$_f$ 0.5) was eluted with 20% aqueous acetonitrile and the eluate concentrated to remove acetonitrile, then lyophilized at 0° to yield carbapenem potassium salt k (1.46 mg by UV, 21% yield).

UV λ$_{max}$ 303 nm
NMR (δ, D$_2$O) CH$_3$ 1.25 (d). 1=CH$_2$ 2.88 (m) H$_6$ 3.44 (dd), H$_5$, H$_8$ 4.25 (m), C$_6$H$_5$ 7.45 (m).

l→m

Step N: Preparation of (5R,6S)-2-(2-aminoethylthio)-6-(R-1-hydroxethyl)-3-(5-tetrazolyl)carbapenem m The blocked carbapenem l (13 mg, 0.020 mmmoles) was deblocked in an exactly analogous fashion to that employed for k to yield 4.4 mmoles (by UV) of tetrazolyl thienamycin m (22% yield).

UV (H$_2$O) λ$_{max}$ 293 nm
NMR (δ, D$_2$O), 1.30 (d) CH$_3$, 3.20 (m)+CH$_2$ and S N, 3.55 (dd H$_6$), 4.35 (m) H$_5$, H$_8$.

n→o

Step O: Preparation of Potassium (5R,6S)-2-cyano-methylthio-6-(R-1-hydroxethyl)-3-(5-tetrazolyl)carbapenem o A mixture of n (0.055 gm, 0.11 mmol), 0.06 gm 10% palladium on carbon, 2 ml 0.1 m dipotassium-hydrogenphosphate/potassium dihydrogenphosphate, pH 7 buffer, 4 ml water, 8 ml tetrahydrofuran, and 2 ml ethanol was hydrogenated at 45 psi hydrogen for one hour. The mixture was filtered through Celite, eluting with water. The filtrate was washed with 50 ml diethylether and concentrated under vacuum to a volume of 3 ml. Reverse phase prep TLC chromatography (5% ethanol in H$_2$O) allowed isolation of a band R$_f$.8. The silica was eluted with 40 ml acetonitrile:water/4:1. Concentration and lyophilization gave 0.030 gm (82%) o as a white powder:

$^1$H NMR (D$_2$O) δ 4.48 (1H, m, J=2.5, 8, 9.5), 4.35 (1H, quintet, J=6.5), 3.92 (2H, AB quartet, J=17), 3.61

(1H, dd, J=2.5, 6.5), 3.48 (1H, AB quartet, J=9.5, 17), 3.37 (1H, AB quartet, J=8, 17), 1.37 (3H, d, J=6.5). UV $\lambda_{max}$ 294 nm.

g→p

Step P: Preparation of (5R,6S)-2-N,N-dimethylcarbamimidoylmethylthio)-6-(R-1-hydroxyethyl)-3-(5-tetrazolyl)carbapenem p 1,8-Diazabicyclo[5.4.0]undec-7-ene (0.029 ml, 0.19 mmol) was added to a solution of g (0.070 gm, 0.16 mmol) and 2 ml dry tetrahydrofuran at −78°. After stirring 20 minutes, 1 mmol) was added. After one hour, the solution was warmed to −20°. Sodium hydrogensulfide (0.011 gm, 0.19 mmol), diisopropylethylamine (0.036 ml, 0.21 mmol), and 1.5 ml dry dimethylformamide were added. The solution was warmed to 0° and stirred for two hours. Chloromethyl, N,N-dimethylcarboxamidine hydrochloride (0.080 gm, 0.52 mmol) and diisopropylethylamine (0.072 ml, 0.42 mmol) were added. The solution was let stand at 0° for 18 hours, then diluted with 150 ml ethylacetate. After washing with 50 ml pH 7 phosphate buffer and 30 ml saturated sodium chloride, the organic layer was dried over magnesium sulfate, filtered, and evaporated to give a brown oil.

This crude product was dissolved in 3 ml tetrahydrofuran, 2 ml ethanol, 1 ml water, and 1 ml 0.1 m pH 7 phosphate buffer. After addition of 70 mg 10% palladium on carbon, the mixture was hydrogenated at 47 psi hydrogen for 1.5 hours. The mixture was filtered through Celite, eluting with water. The filtrate was washed wih 30 ml diethylether and concentrated under vacuum to a volume of 2 ml. Reverse phase prep TLC chromatography (10% ethanol in water) allowed isolation of a band at $R_f$.3. The silica was eluted with 20 ml acetonitrile:water/4:1. Concentration and lyophylization gave 0.009 gm p as an off-white powder:

$^1$H NMR (D$_2$O) δ 4.45–4.30 (2H, m), 3.84 (2H, br s), 3.60 (1H, m), 3.22 (2H, m), 3.12 (3H, s), 2.74 (3H, s), 1.32 (3H, d, J=7). UV $\lambda_{max}$ 289 nm.

EXAMPLE 3

Preparation of Pharmaceutical Compositions

One such unit dosage form is prepared by mixing 120 mg of the compound of Example 1 (Compound A) with 20 mg of lactose and 5 mg of magnesium stearate and placing the 145 mg mixture into a No. 3 gelatin capsule. Similarly, by employing more of the active ingredient and less lactose, other dosage forms can be put up in No. 3 gelatin capsules, and, should it be necessary to make more than 145 mg of ingredients together, larger capsules such as compressed tablets and pills can be prepared. The following examples are illustrative of the preparation of pharmaceutical formulations:

| TABLET | PER TABLET |
|---|---|
| Compound A | 125 mg. |
| Cornstarch, U.S.P. | 6 mg. |
| Dicalcium Phosphate | 192 mg. |
| Lactose, U.S.P. | 190 mg. |
| Magnesium Stearate | Balance/800 mg. |

The active ingredient is blended with the dicalcium phosphate, lactose and about half of the cornstarch. The mixture is then granulated with 15% cornstarch paste (16 mg) and rough-screened. It is dried at 45° C. and screened again through No. 16 screens. The balance of the cornstarch and magnesium stearate is added and the mixture is compressed into tablets, approximately 0.5 inch in diameter each weighing 800 mg.

| | PER TABLET |
|---|---|
| PARENTERAL SOLUTION | |
| Ampoule: | |
| Compound A | 500 mg |
| Diluent: Sterile Water for Injection | 2 cc. |
| OPHTHALMIC SOLUTION | |
| Compound A | 100 mg. |
| Hydropropylmethyl Cellulose | 5 mg. |
| Sterile Water to | 1 ml. |
| OPTIC SOLUTION | |
| Compound A | 100 mg. |
| Benzalkonium chloride | 0.1 mg. |
| Sterile Water to | 1 ml. |
| TOPICAL OINTMENT | |
| Compound A | 100 mg. |
| Polyethylene Glycol 4000 U.S.P. | 400 mg. |
| Polyethylene Glycol 400 U.S.P. | 1.0 gram |

Similar composition can be prepared with Formula I compounds where Z is other than (CH$_2$)$_2$—NH$_2$.

What is claimed is:

1. The compound

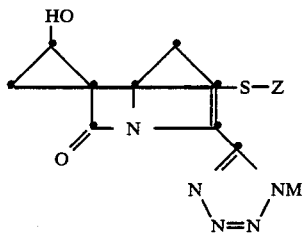

wherein Z is C$_1$-C$_3$ alkylamino, C$_1$-C$_3$ alkylguanidino, C$_1$-C$_3$ alkylamidino, or N-pyrrolidinyl, M is H or a pharmaceutically acceptable cation selected from sodium and potassium.

2. The compound of claim 1 wherein Z is

—(CH$_2$)$_2$—NH$_2$, —(CH$_2$)$_2$—N=C(NH$_2$)—H, —CH$_2$—C(=NH)—N(CH$_3$)$_2$ or

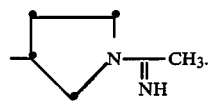

3. An antibiotic composition comprising a therapeutically effective amount of a compound according to claim 1 and a pharmaceutically effective carrier therefor.

4. An antibiotic method of treatment comprising administering a therapeutically effective amount of a compound according to claim 1.

* * * * *